US007628534B2

(12) United States Patent  
Deoclezian et al.

(10) Patent No.: US 7,628,534 B2
(45) Date of Patent: Dec. 8, 2009

(54) THERMAL EROSION TEST DEVICE AND METHOD FOR TESTING THERMAL PROTECTION MATERIALS OF SOLID PROPELLANT THRUSTERS

(75) Inventors: Jean-Marc Deoclezian, St Medard en Jalles (FR); Frédéric Plazanet, Arsac (FR); Caroline Nguyen, Chilly-Mazarin (FR); Vincent Bodart, Paris (FR)

(73) Assignees: Snecma Propulsion Solide, Le Haillan (FR); SNPE Materiaux Energetiques, Paris (FR)

( * ) Notice: Subject to any disclaimer, the term of this patent is extended or adjusted under 35 U.S.C. 154(b) by 0 days.

(21) Appl. No.: 12/004,461

(22) Filed: Dec. 19, 2007

(65) Prior Publication Data

US 2008/0192799 A1 Aug. 14, 2008

(30) Foreign Application Priority Data

Dec. 21, 2006 (FR) .................................. 06 55802

(51) Int. Cl.
*G01N 25/00* (2006.01)
*G01N 17/00* (2006.01)
*G01K 7/00* (2006.01)

(52) U.S. Cl. ............................. 374/7; 374/5; 374/141; 374/163; 374/57

(58) Field of Classification Search ............ 374/5, 374/7, 57, 163, 141
See application file for complete search history.

(56) References Cited

U.S. PATENT DOCUMENTS

| 3,165,924 | A | * | 1/1965 | Wolff ...................... 73/112.01 |
| 3,391,102 | A | | 7/1968 | Major |
| 3,404,557 | A | * | 10/1968 | Hecht et al. ...................... 73/7 |
| 4,523,475 | A | * | 6/1985 | Bills et al. ...................... 73/781 |
| 4,561,784 | A | * | 12/1985 | Benz et al. ...................... 374/8 |
| 4,759,215 | A | * | 7/1988 | Atchley et al. ................ 73/167 |
| 5,113,650 | A | * | 5/1992 | Junior et al. .................. 60/253 |
| 5,419,116 | A | * | 5/1995 | Rast et al. ..................... 60/204 |
| 5,419,119 | A | * | 5/1995 | Obney ......................... 60/253 |
| 6,054,521 | A | | 4/2000 | Nelson |

OTHER PUBLICATIONS

Cauty, F. Ultrasonic Method Applied to Full-Scale Solid Rocket Motors, Journal of Propulsion and Power, American Institute of Aeronautics and Astronautics, New York, NY, US, vol. 16, No. 3, May 2000, pp. 523-528, XP000935381, Issn: 0748-4658.

* cited by examiner

*Primary Examiner*—Gail Verbitsky
*Assistant Examiner*—Mirellys Jagan
(74) *Attorney, Agent, or Firm*—Weingarten, Schurgin, Gagnebin & Lebovici LLP

(57) ABSTRACT

The invention relates to a thermal erosion test device for testing thermal protection materials for use in a solid propellant thruster. The device comprises a support for holding a plate made of the thermal protection material for testing so that its faces a face of a block of solid propellant, the space between the plate and the face of the propellant block defining a combustion chamber of substantially rectangular shape, said chamber extending along said plate and opening out into a nozzle.

13 Claims, 6 Drawing Sheets

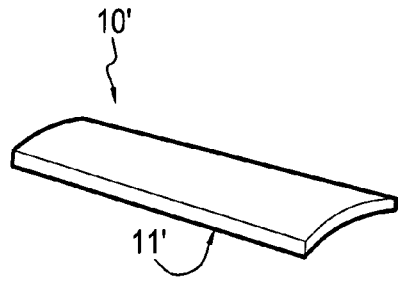
FIG.2
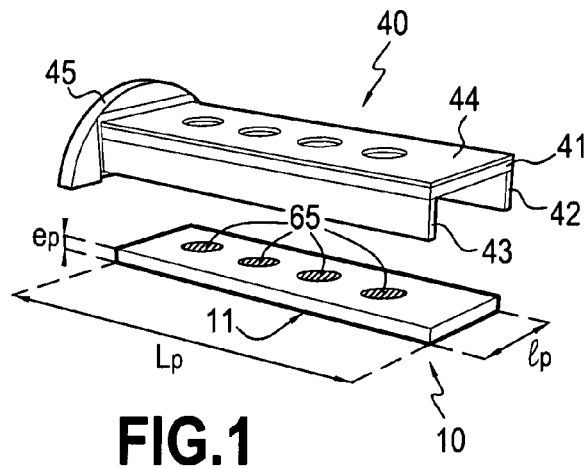
FIG.1
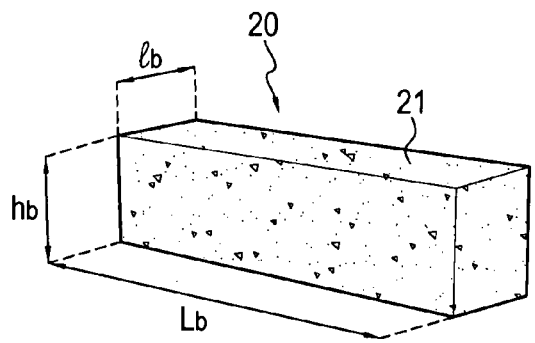
FIG.3A  FIG.3B
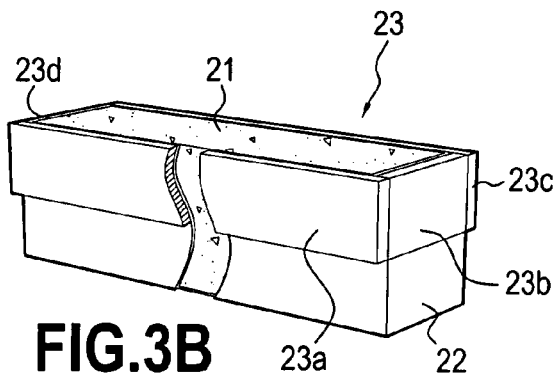
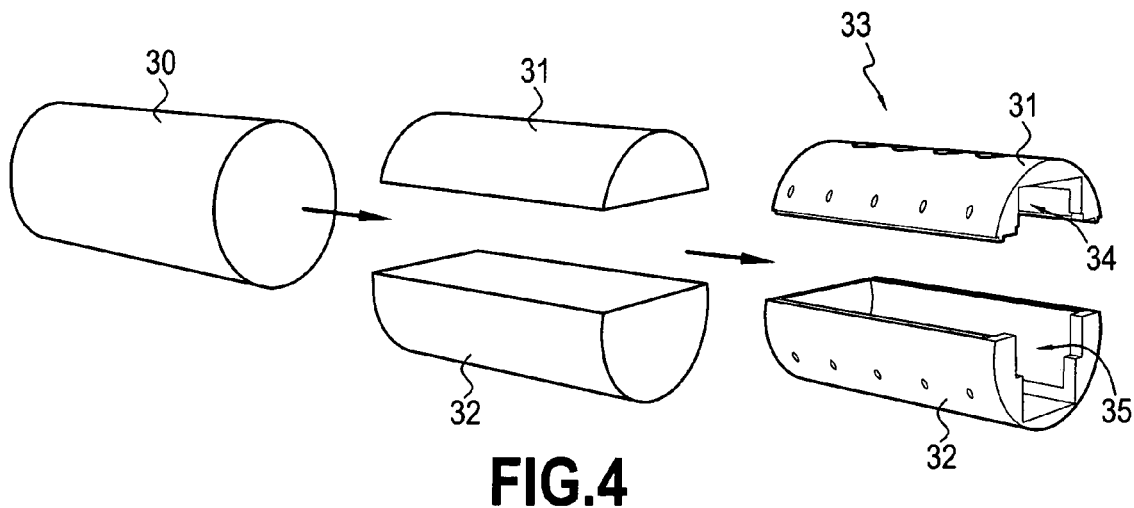
FIG.4

THERMAL EROSION TEST DEVICE AND METHOD FOR TESTING THERMAL PROTECTION MATERIALS OF SOLID PROPELLANT THRUSTERS

This application claims priority to French application No. 06 55802 filed Dec. 21, 2006.

BACKGROUND OF THE INVENTION

The present invention relates to the field of thermal protection materials for use in solid propellant thrusters. More precisely, the invention relates to tests and modeling means suitable for characterizing the thermal erosion behavior of thermal protection made using such materials under conditions that are representative of those to which they will be subjected in a full-sized thruster, i.e. at 1/1 scale.

The performance of thermal protection is evaluated as a function of its thermal erosion behavior in response to the gas generated by the combustion of the solid propellant. During combustion of the propellant in the thruster, under the effect of the high temperatures those portions of the thermal protection material that are exposed to the flow of combustion gas become degraded on the surface by forming coke, and the coke as formed in this way is subjected to erosion to a greater or lesser extent as a function of the degree of its exposure to the flow and of the speed of the flow. The thermal erosion behavior of a thermal protection material corresponds to evaluating its ability to withstand the temperatures and the aerodynamic forces encountered in the thruster.

One of the methods presently in use for characterizing the thermal erosion behavior of internal thermal protection for solid propellant thrusters consists in a modeling tool based on a semi-empirical relationship (erosion criterion) defined on the basis of experimental results obtained when testing 1/1 scale thrusters and for a specific type of material. Consequently, the modeling tool developed can be used only for characterizing the thermal erosion behavior of thermal protection made out of the material with which the 1/1 scale tests were performed.

Nevertheless, in order to improve the thermal erosion behavior of thermal protection internal to thrusters so as to reduce cost and/or weight, it is desirable to develop novel thermal protection making use of novel materials corresponding either to materials of a different kind, or to materials of the same kind but to which significant advances have been applied. Either way, the model available for thermal erosion calculation is not usable since it is based on an erosion criterion defined from a specific material. Consequently, for each new material, it is necessary to perform one or more tests at 1/1 scale in order to determine an erosion criterion and to have a calculation model that matches the characteristics of the material in question.

This need to perform one or more tests at 1/1 scale prevents performing prior studies at low cost that would make it possible to evaluate the improvements (in terms of performance and cost) that might be obtained by using a new material, and prevents dimensioning of thermal protection to be made with the new material in a thruster by calculation (modelization) at 1/1 scale.

Consequently, there exists a need to enable tests to be performed at lower cost, i.e. at a small scale, thus making it possible to avoid any need to perform test firings at 1/1 scale.

Existing reduced scale test means in use for characterizing the thermal erosion behavior of thermal protection materials make use of cylindrical extenders of small diameter (about 200 millimeters (mm)). However inspecting those tests show that the appearance of cokefied material and erosion levels found during such tests differ from those observed on thrusters at 1/1 scale. Although such tests make it possible to carry out comparative studies between two materials, they are not representative of behavior at 1/1 scale, and consequently they cannot be used for devising a calculation model that can be used for evaluating and dimensioning thermal protection for use in a thruster at 1/1 scale.

OBJECT AND SUMMARY OF THE INVENTION

An object of the present invention is to provide reduced scale test means suitable for characterizing the thermal erosion behavior of a thermal protection material, said behavior being representative of the behavior of thermal protection making use of said material in a 1/1 scale thruster.

To this end, the present invention provides a thermal erosion test device for testing thermal protection materials for use in a solid propellant thruster, the device comprising means for holding a plate made of the thermal protection material for testing so that its faces a face of a block of solid propellant, the space between the plate and the face of the propellant block defining a combustion chamber of substantially rectangular shape, said chamber extending along said plate and opening out into a nozzle.

The test device of the present invention thus makes it possible to expose a plate of thermal protection material to a tangential flow of combustion gas generated by a block of propellant placed facing said plate. This configuration makes it possible to carry out tests under conditions that are close to those of 1/1 scale. The Applicant has found that using a plane plate for the material under test in a device defining a flow stream that is of substantially rectangular section and that extends along the plate makes it possible to reproduce conditions that are close to those encountered by internal thermal protection in thrusters, in particular because of the fact that radii of curvature are large at 1/1 scale.

In prior art test means using cylindrical extenders, the radii of curvature are small. The thermal erosion behavior of thermal protection in such test means is different from that at 1/1 scale, in particular because of "edge effects" that lead to coke formation (structuring) and to coke erosion on the thermal protection that are different from those observed at 1/1 scale, where such effects are of little significance.

Consequently, the use of a plate is much more representative of a portion of internal thermal protection at 1/1 scale placed in a thruster presenting a large radius of curvature.

In addition, the combustion chamber of the test device of the invention extends along the plate of material under test that itself faces the block of propellant. This configuration serves to have different levels of stress on the exposed face of the plate, since the flow of combustion gas from the block of propellant is greater and faster on getting closer to the gas ejection nozzle. It is thus possible, at different locations distributed along the length of the plate, to have different stress zones that are directly representative of certain portions of the thruster.

According to an aspect of the invention, the device includes means for measuring the variation in the degradation and the retreat of the surface of the plate of thermal protection material for testing.

The device may include a plurality of ultrasound sensors disposed along the plate of thermal protection material for testing, said sensors being coupled with said plate by a coupling material. These sensors make it possible to track the degradation front in the material throughout a test firing and to do so at different locations along the plate corresponding to zones of different stresses. In addition, the device may comprise a plurality of plasma capacitance gauges disposed along the plate of thermal protection material for testing in order to measure how the material retreats in the different stress zones during a test firing.

According to another aspect of the invention, the plate of thermal protection material for testing includes a plurality of temperature-measurement sensors disposed along said plate. These sensors may be distributed along the plate in a plurality of groups, each sensor in a group of sensors being implanted at a determined depth in the thickness of the plate. This makes it possible to measure the different levels of thermal stress to which the plate is subjected, both through its thickness and along its length.

The measurements collected with such instrumentation can be used for accurately characterizing the thermal erosion behavior of the material under test, to define conditions for subsequent tests by adjusting stress levels, and to devise calculation methods for use in dimensioning thermal protection at 1/1 scale.

According to yet another aspect of the invention, the test device includes means for adjusting the distance between the block of solid propellant and the plate of thermal protection material for testing. In this way, the levels of aerothermal stresses within the device can be set merely by adjusting the height of the combustion chamber, thus making it possible in particular to conserve a level of stress that is similar from one test firing to another by setting the operating pressure by means of the diameter of the throat of the nozzle.

The thermal erosion test device of the present invention further includes a cylindrical shell having an inside volume in which the plate of thermal protection material for testing and the block of solid propellant are placed. Thus, by taking the assembly of rectangular shape made up of the plate of material for testing and the block of propellant, and placing said assembly within a shell that is cylindrical in shape, it is possible to establish operating pressures that are representative of the operating range of thrusters at 1/1 scale. Obtaining such pressure levels with a purely rectangular shape would require metal plate thicknesses for withstanding pressure forces that are unacceptable, whether in terms of weight or in terms of cost. The use of a shell in accordance with the invention gives the setup an outside shape that is cylindrical, thereby enabling the pressure forces generated therein to be distributed uniformly, and thus enabling it to be placed in a metal tube of reasonable thickness.

The tube in which the setup with the shell is placed is itself closed at its ends by a front end wall and a rear end wall, the rear end wall including the nozzle of the test device which is connected to the combustion chamber defined by the space between the plate under test and the facing face of the block of propellant.

The faces of the block of solid propellant other than those facing the plate of thermal protection material for testing are preferably covered in an inhibitor material so as to ensure constant front combustion facing the plate of thermal protection material.

BRIEF DESCRIPTION OF THE DRAWINGS

Other characteristics and advantages appear from the following description of particular embodiments of the invention, given as non-limiting examples, with reference to the accompanying drawings, in which:

FIG. 1 is a perspective view of a plate of thermal protection material for use in the thermal erosion test device in an embodiment of the invention;

FIG. 2 is a perspective view of a variant embodiment of the plate of thermal protection material shown in FIG. 1;

FIGS. 3A and 3B show how a solid block of propellant is prepared for use in the thermal erosion test device in an embodiment of the invention;

FIG. 4 shows how a cylindrical shell is made for the thermal erosion test device of the invention;

DETAILED DESCRIPTION OF EMBODIMENTS OF THE INVENTION

Figure 5:
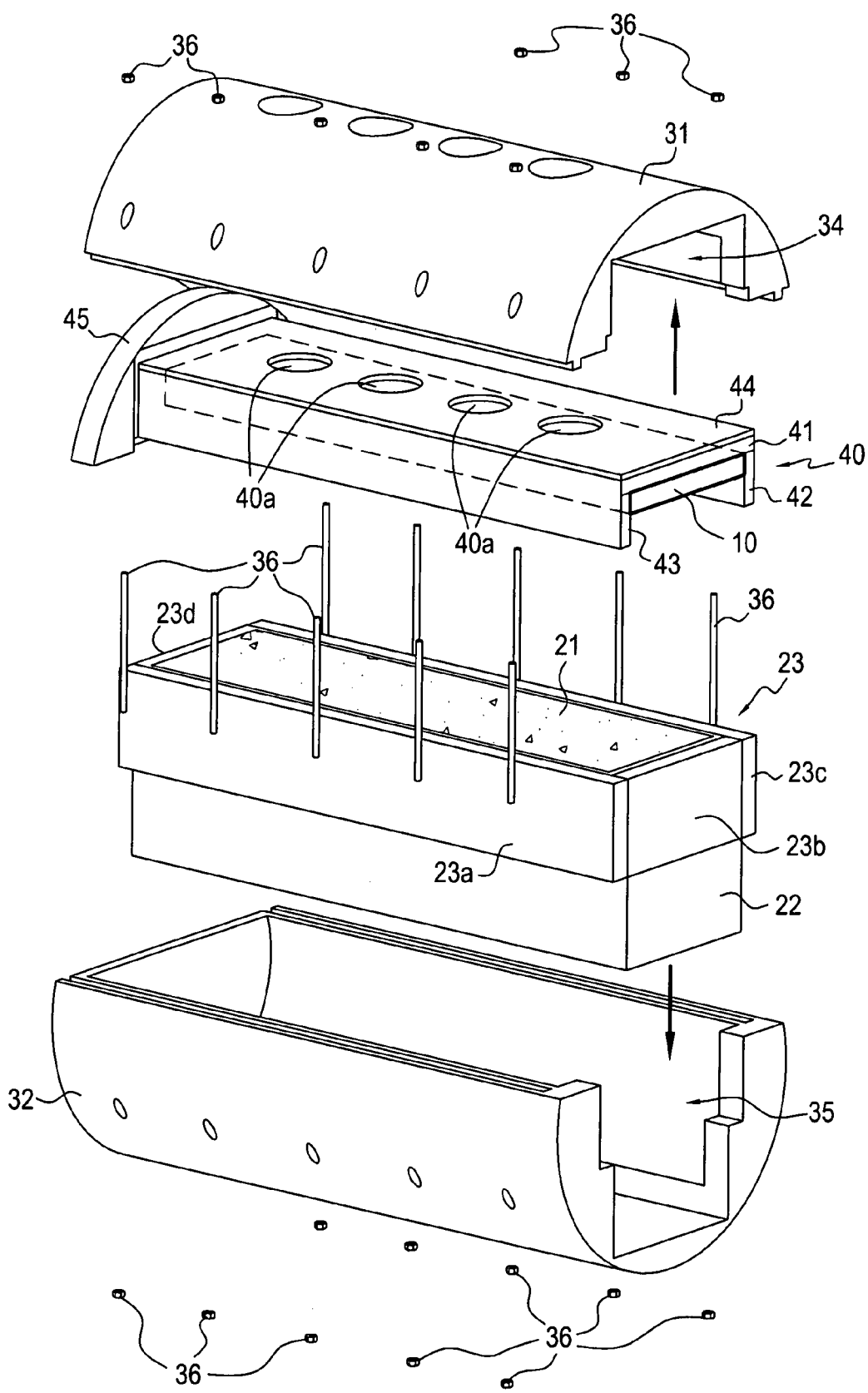
FIG. 5 is an exploded perspective view showing the assembly of a plate of thermal protection material and of a propellant block in the cylindrical shell of FIG. 4.

The principle of the thermal erosion test device of the present invention is to subject a sample of thermal protection material to a tangential flow of combustion gas generated by a rectangular block of solid fuel placed facing the sample.

According to an aspect of the invention, the sample of thermal protection material for testing is made in the form of a plate. FIG. 1 shows a plate thermal protection material 10 forming the sample of thermal protection material for testing in the device of the invention. The plate 1 is preferably of a shape that is sufficiently plane to approximate to the large radii of curvature that are to be encountered in thrusters at 1/1 scale. This plane shape is the simplest to make and makes it easier to incorporate measurement means as described below and also easier to run the test. Nevertheless, as shown in FIG. 2, the plate 10' of thermal protection material may equally well present a small amount of curvature. In general, the face 11 (or 11') of the plate 10 (or 10') that is to be placed facing the combustion face of the propellant block co-operates therewith to form a combustion chamber that is rectangular (when the plate 10 is plane) or substantially rectangular (when the plate 10' is slightly curved).

The length and the width of the combustion chamber formed in the device between the plate and the propellant block corresponds to the length and the width of the plate 10 of thermal protection material. The plate 10, and consequently the combustion chamber, may present by way of example a length $L_p$ of about 800 mm and a width $l_p$ of about 150 mm. These fixed dimensions are defined as a function of a compromise between being representative of 1/1 scale and the constraints of making the device. The dimensions could be greater, but tests have shown that a length of 800 mm and a width of 150 mm are indeed representative of the 1/1 scale. The plate 10 also presents a thickness $e_p$ of about 30 mm.

On its top face, the plate 10 is fitted with plasma capacitance gauges 65 that operate in a manner described below. The plate 10 is mounted on a support 40 that has a semicircular front wall 45 and three plane walls 42, 43, and 44. The plate 10 is also bonded in the support 10 onto a coupling material 41 that performs a function that is described below. In a variant, the walls 42, 43, and 44 may be made directly out of the coupling material, in which case the coupling material 41 is no longer needed.

FIG. 3A shows a solid propellant block 20 of rectilinear shape that is for placing in the device of the invention so as to place the plate 10 of thermal protection material. The propellant block 20 presents a length $L_b$ and a width $l_b$ that are substantially identical to the length and the width of the plate of thermal protection material. The height $h_b$ of the block is defined as a function of the duration of the test firing that is to be performed. By way of example, the propellant block may have a length $L_b$ of about 800 mm, a width $l_b$ of about 150 mm, and a height of $h_b$ of about 205 mm, which corresponds to a propellant charge of about 50 kilograms (kg).

As shown in FIG. 3B, the propellant block is then prepared. More precisely, the face 21 of the propellant block 20 that is to be placed facing the face 11 of the plate 10 constitutes the only combustion face of the block. The other faces of the block 20 are covered in an inhibitor material 22, such as a oxamide-filled polyurethane finishing varnish so as to privilege front combustion of the block and conserve a constant combustion area during firing. An inhibited propellant block 23 is thus obtained. Reinforcing plates 23a to 23d are also placed around at least around the top portion of the block 23.

The level of operating pressure in the device of the invention needs to be sufficiently high in order to be representative of 1/1 scale. The pressure in the device varies over the range about 2 megapascals (MPa) to 12 MPa. Nevertheless, in order to withstand such pressure levels, retaining a rectangular shape for the entire setup would require making use of thicknesses of metal plate that would be unacceptable in terms of weight and expense.

For this purpose, the device of the invention proposes bringing the outside shape of the device into a cylindrical shape, making use of a shell that forms a packing structure for filling the space between the assembly comprising the propellant block and the plate of thermal protection material in which the rectangular combustion chamber is formed, and the outer tube or shroud of the device. More precisely, as shown in FIG. 4, a shell 33 is made from a cylinder 30, e.g. made of cold-castable polyurethane varnish that is machinable. The cylinder 30 is then split into two half-shells 31 and 32 and the inside thereof is machined so as to form respectively a housing 34 for the plate of thermal protection material and a housing 35 for the block of propellant.

Figure 6:
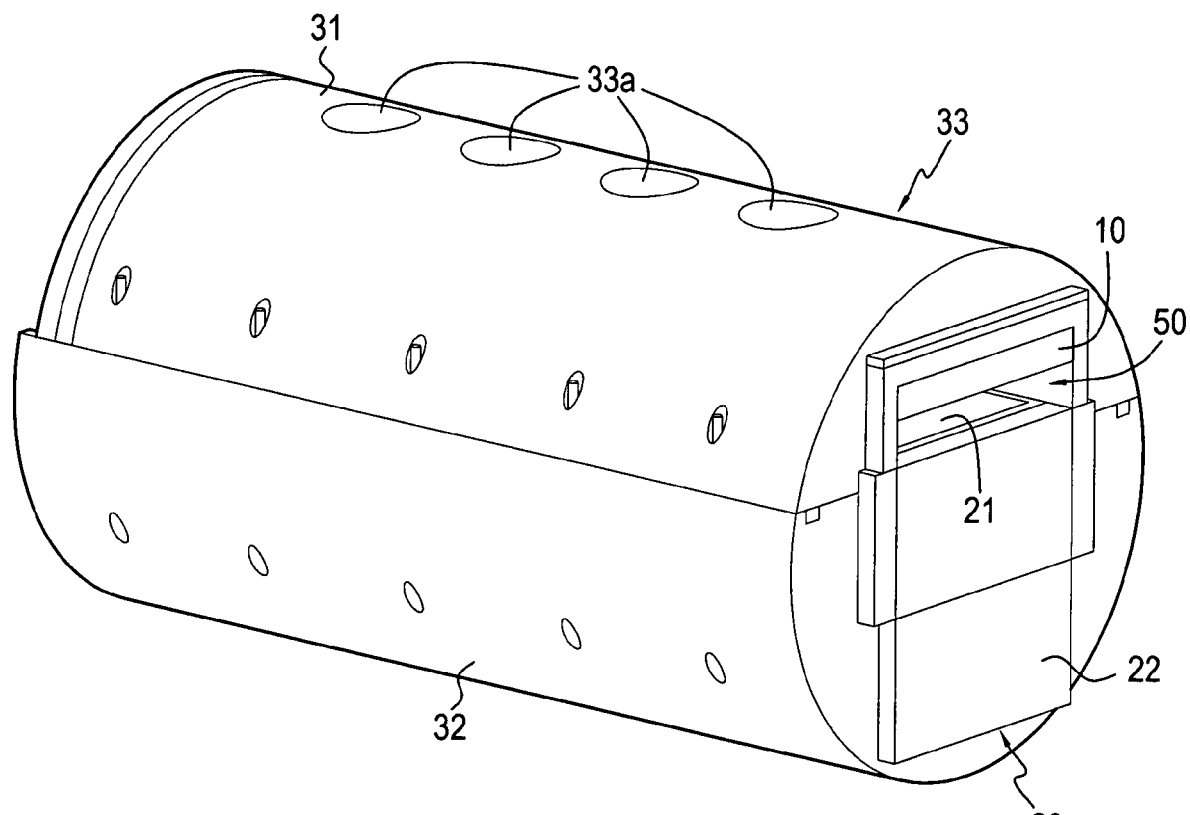
FIG. 6 shows the elements of FIG. 5 once they have been assembled together.

FIG. 5 shows how the plate of thermal protection material and the block of propellant assembled inside the cylindrical shell 33. The inhibited propellant block 23 is housed in the volume 35 of the first half-shell 32, while the plate 10 of thermal protection material mounted on the support 40 is placed in the volume 34 of the second half-shell 31. The two half-shells 31 and 32 are assembled together and held one against the other by a system of metal tie-bars and nuts 36. Once the half-shells have been assembled together, as shown in FIG. 6, the plate 10 of thermal protection material is held inside the cylindrical shell 33 facing the inhibited propellant block 23, with the space between the plate 10 and the block 23 defining a combustion chamber 50 of rectangular shape. The inhibited propellant block 23 is not bonded to the half-shell 32. Clearance of about 1 mm exists between the block and the half-shell, thus making it possible with arrangements in the half-shells to ensure that the arrangement elements inside the device are put at equal pressures.

Figure 7:
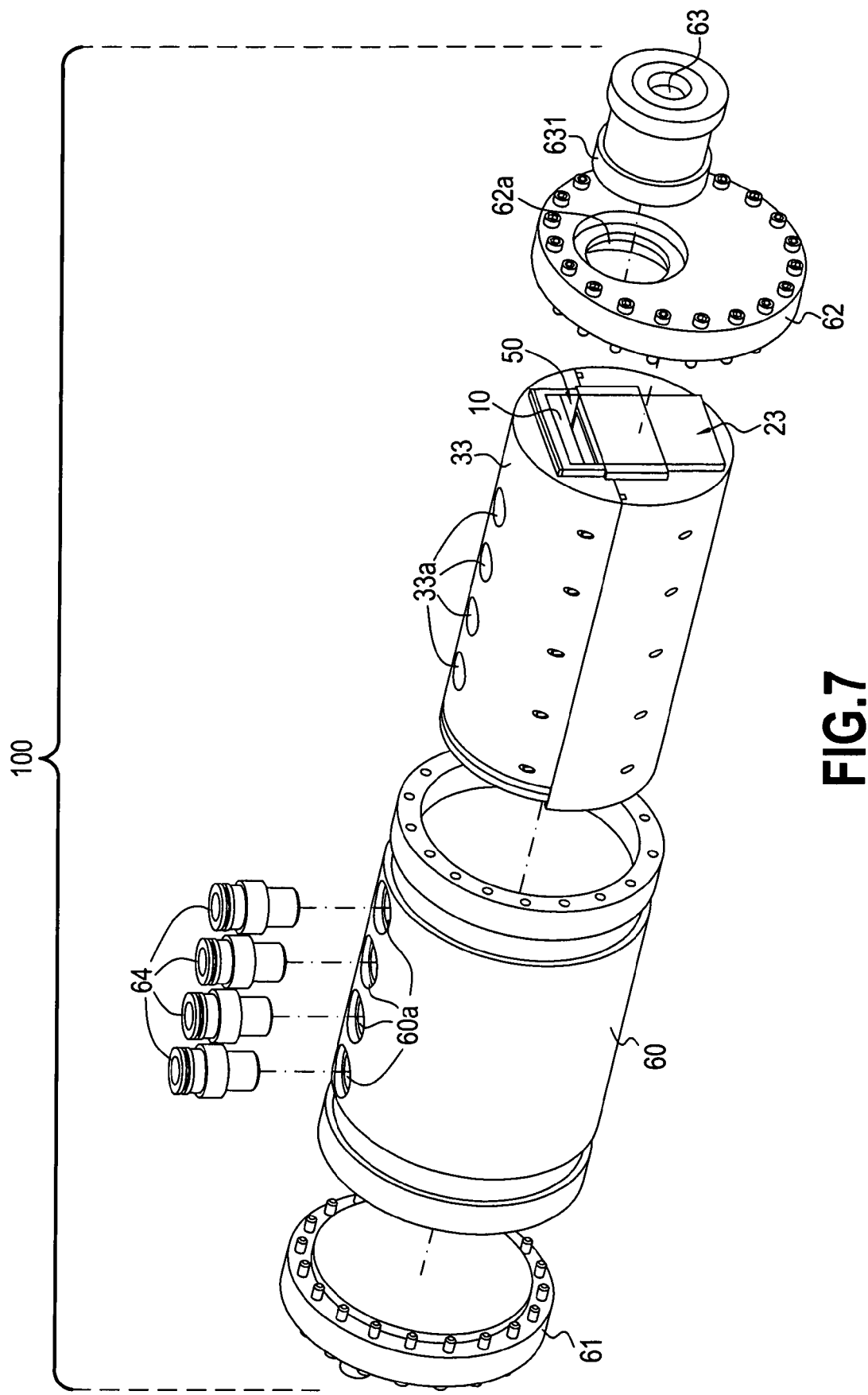
FIG. 7 is an exploded perspective view showing the assembly of a thermal erosion test device in an embodiment of the invention.
Figure 8:
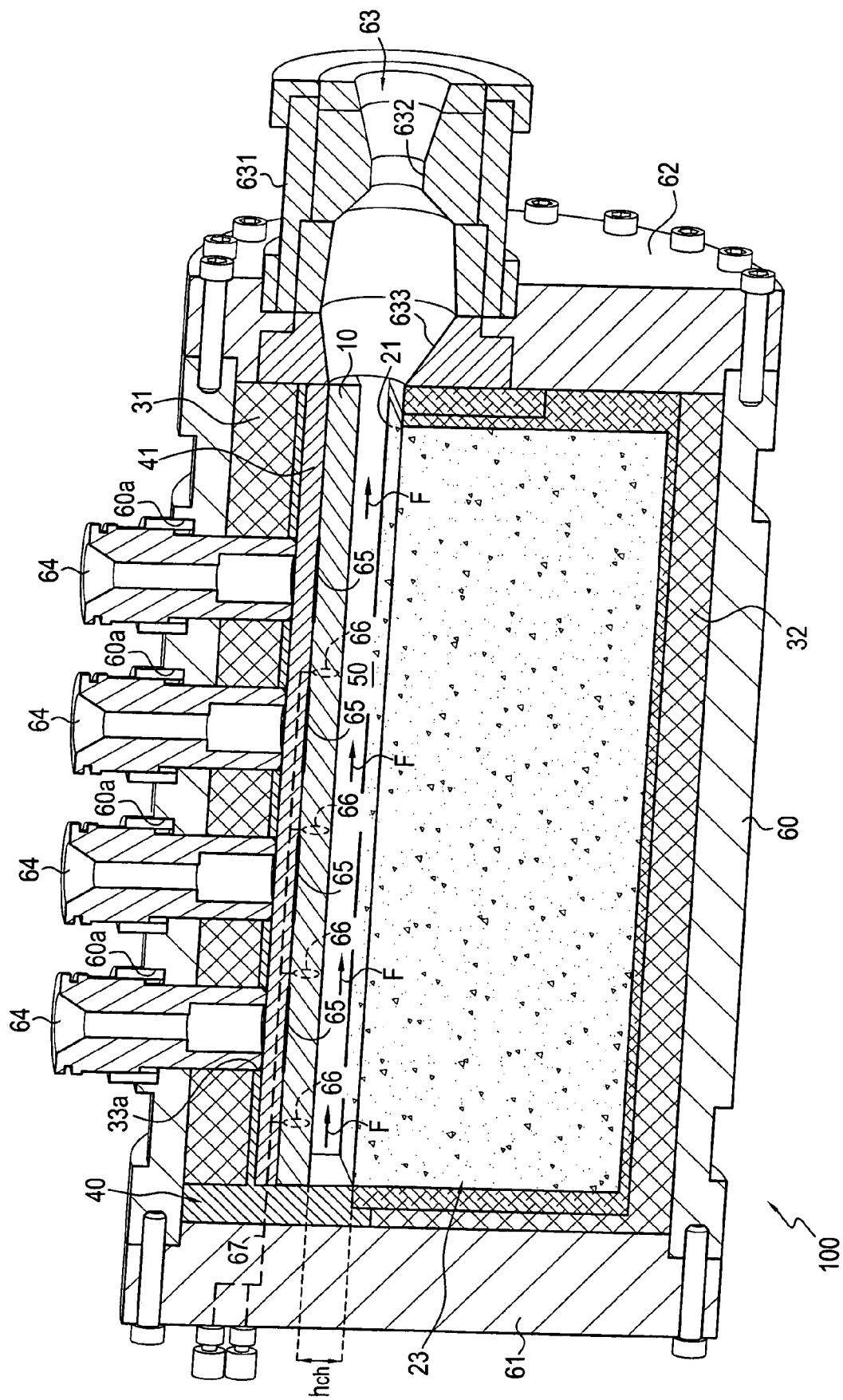
FIG. 8 is a section view of the thermal erosion test device after the element of FIG. 7 has been assembled together.

FIG. 7 shows the assembly of a test device 100 of the invention by placing the cylindrical shell 33 containing the plate of thermal protection material and the block of inhibited propellant inside a metal shroud or tube 60 that is closed at its ends by a front end wall 61 and a rear end wall 62 having an opening 62a to which there is connected a nozzle port 631 of a nozzle 63. The tube 60 has openings 64a for co-operating with openings 33a in the cylindrical shell 33 so as to enable ultrasound sensors 64 to be mounted inside the device. Once the test device 100 has been assembled as shown in FIG. 8, the combustion chamber 50 formed between the plate 10 of thermal protection material and the propellant block 23 opens out into the nozzle 63. The gas generated by the combustion of the propellant block 23 flows into the combustion chamber 50 in a flow direction represented by arrows F. The rectangular shape of the combustion chamber 50 is matched to the nozzle 63 via a cylindro-conical ring 633. The pressure in the combustion chamber 50 is adjusted as a function of the diameter of the throat 632 of the nozzle 63. The materials used for the test device 100 are selected to withstand temperatures up to at least 3500 K.

The level of aerothermal stress to which the plate 10 of thermal protection material is subjected is a function of the height of the combustion chamber $h_{ch}$. The height $h_{ch}$ is set by adjusting the height of the propellant block 23. When it is desired to perform a plurality of firings having the same duration but different levels of stress, a moving bottom is used under the propellant block (not shown in the figures) making it possible to use blocks that are all of the same height (i.e. that present the same firing duration) but that are positioned closer to or further from the plate of thermal protection material for testing, depending on whether it is desired to increase or reduce the level of aerothermal stress.

The test device of the invention is also fitted with sensors for measuring various parameters suitable for characterizing the thermal erosion behavior of the plate of thermal protection material for testing.

As shown in FIG. 8, the device has ultrasound sensors 64 serving to measure variation in the degradation front of the plate of thermal protection material. To enable ultrasound waves in the plate 10 of thermal protection material to propagate without risk of damaging the sensors, the support 40 of the plate 10 comprises a coupling material 41 interposed between the plate 10 and the sensors 64. The support 40 also includes openings 40a co-operating with the openings 33a and 60a respectively in the cylindrical shell 33 and the tube 60, thus enabling the sensors 64 to be placed in contact with the coupling material 41. Each ultrasound sensor 64 emits a sinewave that is reflected in part on each interface of material characterized by a change in acoustic impedance (coupling material to thermal protection material, good thermal protection material to coke, and coke to combustion gas). The sensor also acts as a receiver of reflected waves, thus making it possible to determine how the path followed by the ultrasound waves through the stack varies over time during the test. Knowing the speed of these waves as a function of temperature, it is possible to determine how the positions of the various interfaces vary over time. It is thus possible to determine the variation in the degradation front (the front of pyrolysis within the thermal protection material) over time during a test firing.

The device of the invention also includes plasma capacitance gauges 65 of working section close to the size of the ultrasound sensors 64 and placed in the same positions as the ultrasound sensors. The principle on which these gauges measure is based on measuring the capacitive impedance of the plate 10 of thermal protection material between two electrodes, the first electrode being constituted by a gauge 65, and the second electrode being constituted by the conductive plasma generated by the combustion gas, which is highly ionized. This impedance measurement can be used for tracking variation in a zone close to the surface 11 of the plate 10 that is exposed to the flow of combustion gas, and to deduce how the retreat of the plate progresses.

The plate 10 of thermal protection material is also provided with temperature sensors 66 disposed therealong at different depths. By way of example, during manufacture of the plate 10 of thermal protection material, 16 temperature sensors, e.g. constituted by thermocouples, are implanted therein to make up four groups of four sections spaced apart along the plate 10 and delivering measurement signals that are conveyed to the front end wall 61 by connections 67. For each section, the four thermocouples are implanted at different depths within the plate. In this way, it is possible to know the temperature of the plate at various locations, and in particular in its thickness, in order to evaluate specifically the amount of thermal insulation it provides over time.

The device includes one or more pressure takeoffs (not shown in the figures) that make it possible in particular to measure pressure in the nozzle and in the combustion chamber.

The test device of the invention also includes an igniter for initiating combusting of the block of propellant, and also one or more pressure safety devices calibrated to trigger at some maximum determined pressure level (not shown in the figures).

Figure 9:
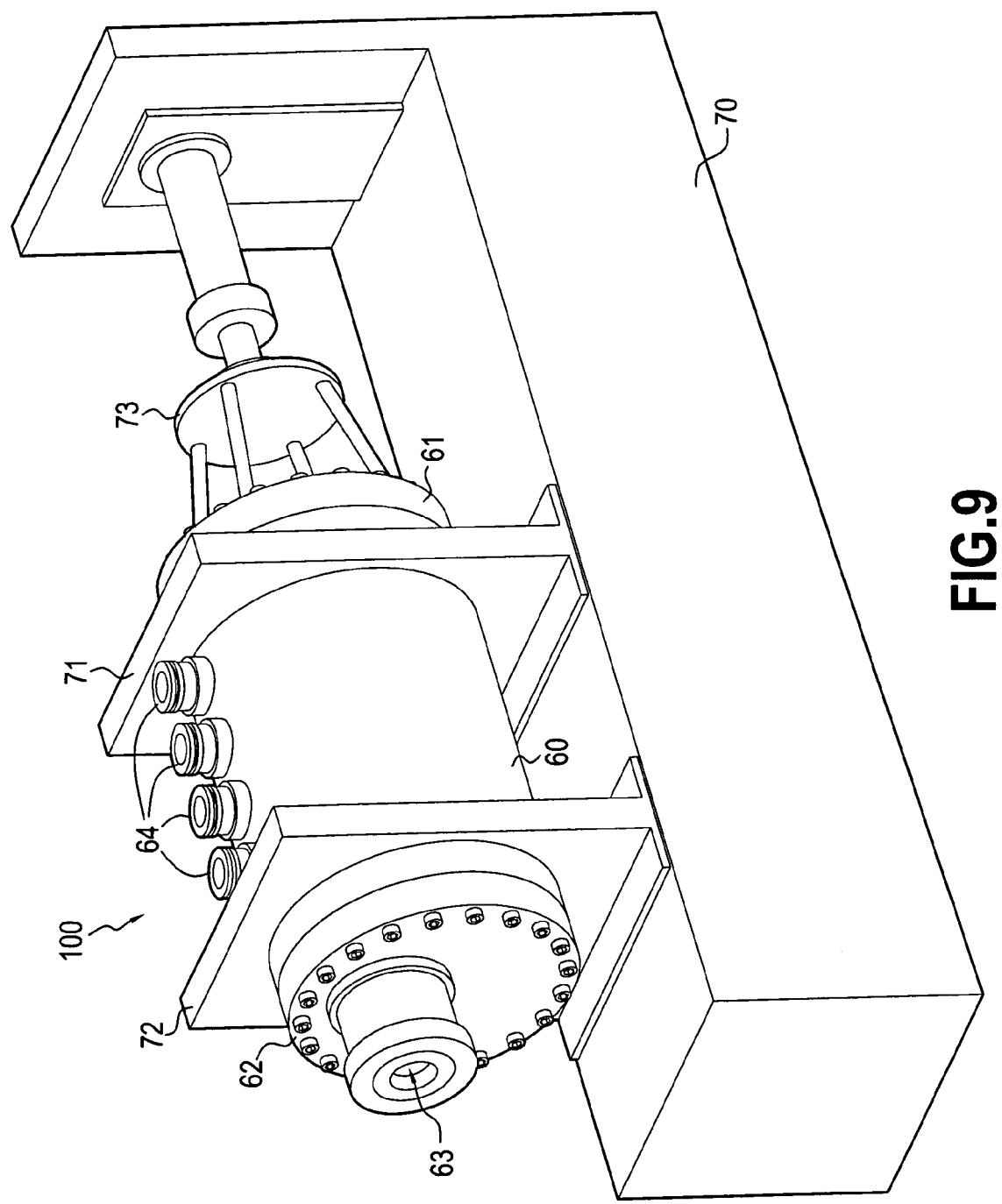
FIG. 9 is a perspective view showing a thermal erosion test device mounted on a test bench.

FIG. 9 shows the test device of the invention installed on a test bench 70. The test bench 70 comprises two elements 71 and 72 supporting the test device of the invention. The device is also held by a system 73 that passes cables for the measurement sensors, the igniter, and the pressure security device(s).

The dimensions and the configuration of the combustion chamber of the test device of the present invention enable the following needs to be satisfied:
- reproducing aerothermal and radiation stresses that are representative of a thruster at 1/1 scale;
- passing through the various stress conditions encountered in a thruster at 1/1 scale during a single test firing:
  - in the first half of the plate, beside the front end wall, stresses are obtained that are typical for shroud and front end wall zones of a thruster; and
  - in the second half of the plate, beside the nozzle, stresses are obtained that are typical of the rear end of a thruster in a deflected configuration.

During test firings carried out with the device of the invention as described above, aerothermal and radiation calculations have enabled the following points to be observed:
- no impacts of particles of alumina against the sample plate of thermal material for testing;
- stress levels (convective flux and parietal shear) on the sample plate representative of all of the conditions encountered by internal thermal protection in 1/1 scale thrusters;
- the existence of a zone on the sample plate that is not influenced by the presence of the side walls of the stream; and
- the absence of any influence of the aluminum in the propellant on the radiation flux received by the plate.

In addition, thermal erosion calculations on a sample plate made of GSM55 have shown that the test device of the invention makes it possible to cover all of the erosion conditions of the material:
- non-erosive or conductive thermal conditions: stresses are thermal only and the coke that is formed stays in place;
- pulsed erosion conditions: an intermediate circumstance in which the coke that forms is eroded in the form of plates; and
- intense erosive conditions: circumstances of extreme flow severity for which the coke that is formed is eroded immediately.

What is claimed is:

1. A thermal erosion test device for testing thermal protection material for use in a solid propellant thruster, the device comprising means for holding a plate made of the thermal protection material for testing so that the plate faces a face of a block of solid propellant, a space between the plate and the face of the propellant block defining a combustion chamber of a substantially rectangular shape, said combustion chamber extending along said plate and opening out into a nozzle.

2. A device according to claim 1, further including means for adjusting a distance between the block of solid propellant and the plate of thermal protection material for testing so as to adjust a level of aerodynamic stresses in the combustion chamber as a function of said distance.

3. A device according to claim 1, wherein the plate of thermal protection material for testing includes a plurality of temperature-measurement sensors disposed along said plate.

4. A device according to claim 3, wherein the plate of thermal protection material for testing includes a plurality of groups of temperature-measurement sensors spaced apart from one another along said plate, each sensor in a group of sensors being implanted at a determined depth in the thickness of the plate.

5. A device according to claim 1, including means for measuring a variation in the degradation and a retreat of the surface of the plate of thermal protection material for testing.

6. A device according to claim 5, including a plurality of ultrasound sensors disposed along the plate of thermal protection material for testing, said sensors being coupled with said plate by a coupling material.

7. A device according to claim 5, including a plurality of plasma capacitance gauges disposed along the plate of thermal protection material for testing.

8. A device according to claim 1, including a cylindrical shell having an inside volume in which there are placed the plate of thermal protection material for testing, and the block of solid propellant.

9. A device according to claim 8, comprising a tube for receiving the cylindrical shell, said tube being closed at its ends by a front end wall and a rear end wall, respectively, the rear end wall including a nozzle connected to the combustion chamber defined by the space between the plate and the face of the facing block of propellant.

10. A device according to claim 8, wherein the faces of the block of solid propellant other than the face facing the plate of thermal protection material for testing are covered in an inhibitor material.

11. A thermal erosion test device for testing thermal protection material for use in a solid propellant thruster, the device comprising:
- a substantially rectangular plate made of said thermal protection material being tested, said material plate having a substantially rectangular first material face;
- a substantially rectangular block of solid propellant having a substantially rectangular first propellant face sized about a same size as said first material face; and
- a support structure coupled to said material plate and arranged to position said first material face opposite, and spaced apart from, said first propellant face,
- wherein a combustion chamber of a substantially rectangular shape is defined between said first material face and said first propellant face.

12. The thermal erosion test device according to claim 11, wherein:
a nozzle is provided at one end of said combustion chamber.

13. The thermal erosion test device according to claim 11, further comprising:

a plurality of temperature-measurement sensors disposed along said plate.

* * * * *

UNITED STATES PATENT AND TRADEMARK OFFICE
CERTIFICATE OF CORRECTION

PATENT NO. : 7,628,534 B2
APPLICATION NO. : 12/004461
DATED : December 8, 2009
INVENTOR(S) : Jean-Marc Deoclezian et al.

It is certified that error appears in the above-identified patent and that said Letters Patent is hereby corrected as shown below:

Column 4, line 50, "$l_p$" should read --$\ell_p$--;

Column 5, line 2, "$l_b$" should read --$\ell_b$--; and

Column 5, line 7, "$l_b$" should read --$\ell_b$--.

Signed and Sealed this

Eleventh Day of May, 2010

David J. Kappos
*Director of the United States Patent and Trademark Office*